United States Patent
Alander et al.

(10) Patent No.: US 11,957,772 B2
(45) Date of Patent: Apr. 16, 2024

(54) PETROLATUM SUBSTITUTION PREPARATION

(71) Applicant: AAK AB (PUBL), Malmö (SE)

(72) Inventors: Jari Alander, Danderyd (SE); Staffan Norberg, Karlshamn (SE); Mette Skovgaard, Hallaryd (SE); Martin Johansson, Mörrum (SE)

(73) Assignee: AAK AB (publ), Malmö (SE)

( * ) Notice: Subject to any disclaimer, the term of this patent is extended or adjusted under 35 U.S.C. 154(b) by 70 days.

(21) Appl. No.: 17/522,358

(22) Filed: Nov. 9, 2021

(65) Prior Publication Data

US 2022/0062127 A1 Mar. 3, 2022

Related U.S. Application Data

(62) Division of application No. 16/466,086, filed as application No. PCT/SE2017/051273 on Dec. 14, 2017, now abandoned.

(30) Foreign Application Priority Data

Dec. 16, 2016 (SE) .................... 1651664-3

(51) Int. Cl.
| | | |
|---|---|---|
| A61K 8/31 | (2006.01) | |
| A61K 8/36 | (2006.01) | |
| A61K 8/37 | (2006.01) | |
| A61K 8/63 | (2006.01) | |
| A61K 8/72 | (2006.01) | |
| A61K 8/81 | (2006.01) | |
| A61K 8/92 | (2006.01) | |
| A61Q 19/00 | (2006.01) | |
| C10M 111/00 | (2006.01) | |
| C10M 173/02 | (2006.01) | |
| C10N 50/10 | (2006.01) | |

(52) U.S. Cl.
CPC ............... *A61K 8/31* (2013.01); *A61K 8/361* (2013.01); *A61K 8/375* (2013.01); *A61K 8/63* (2013.01); *A61K 8/72* (2013.01); *A61K 8/8111* (2013.01); *A61K 8/922* (2013.01); *A61Q 19/00* (2013.01); *C10M 111/00* (2013.01); *C10M 173/02* (2013.01); *A61K 2800/48* (2013.01); *C10M 2205/026* (2013.01); *C10M 2205/028* (2013.01); *C10M 2205/18* (2013.01); *C10M 2207/022* (2013.01); *C10M 2207/281* (2013.01); *C10M 2207/40* (2013.01); *C10N 2050/10* (2013.01)

(58) Field of Classification Search
CPC .......... A61K 8/31; A61K 8/361; A61K 8/375; A61K 8/63; A61K 8/72; A61K 8/8111; A61K 8/922; A61K 2800/48; A61Q 19/00; C10M 111/00; C10M 173/02; C10M 2205/026; C10M 2205/028; C10M 2205/18; C10M 2207/022; C10M 2207/281; C10M 2207/40; C10N 2050/10
See application file for complete search history.

(56) References Cited

U.S. PATENT DOCUMENTS

| | | | | |
|---|---|---|---|---|
| 4,604,281 | A * | 8/1986 | Deckner | ............... A61Q 1/02 424/59 |
| 4,883,684 | A * | 11/1989 | Yang | ................. A23D 9/00 426/607 |
| 5,660,865 | A * | 8/1997 | Pedersen | ............. A61K 8/925 426/601 |
| 8,524,211 | B1 | 9/2013 | Rafiee et al. | |
| 2004/0170711 | A1* | 9/2004 | Sadek El Mogy | ..... A61P 17/08 424/757 |
| 2011/0280969 | A1 | 11/2011 | Remington et al. | |
| 2012/0045405 | A1* | 2/2012 | Gilman | ............... A61K 8/345 424/62 |
| 2012/0064022 | A1* | 3/2012 | Wray | ................. C08G 77/50 510/238 |
| 2013/0005808 | A1* | 1/2013 | Kachi | ................. A61K 8/37 514/547 |
| 2013/0189207 | A1* | 7/2013 | Blomberg | ............ A61K 8/27 424/769 |
| 2013/0272988 | A1 | 10/2013 | Liu et al. | |

(Continued)

FOREIGN PATENT DOCUMENTS

DE     20 2005 019 454 U1     7/2006

OTHER PUBLICATIONS

Ames et al. ("Structure of the Triterpenes: an Inter-relationship between the Lupeol and the ~—Amyrin Series," in Nature, Dec. 24, 1949, vol. 164). (Year: 1949).*

(Continued)

*Primary Examiner* — Blessing M Fubara
(74) *Attorney, Agent, or Firm* — Finnegan, Henderson, Farabow, Garrett & Dunner, LLP

(57) ABSTRACT

There is provided a petrolatum substitute. The petrolatum substitute preparation comprises 1-20 wt % of at least one oil thickening agent, 7-40 wt % of at least one structuring agent, 0.5-10 wt % of at least one phytosterol or ester thereof, and 30-92 wt % of at least one emollient, wherein the preparation has a melting point of 35° C. or more. The petrolatum substitute preparation can be used in essentially all applications where petrolatum is used today. The substitute can be made renewable and the use of over-exploited natural products is minimized. The preparation is less irritant and has excellent moisture barrier properties when applied to human skin. Further it is less energy consuming to manufacture.

44 Claims, No Drawings

(56) References Cited

U.S. PATENT DOCUMENTS

2013/0331400 A1* 12/2013 Kusakari ................ A61P 37/08
514/257
2014/0302161 A1    10/2014 Bauer et al.
2016/0081968 A1*  3/2016 Svensson ................ A61K 9/06
424/618
2016/0346294 A1* 12/2016 Sengupta ............... A61K 47/32

OTHER PUBLICATIONS

IKuta Yuzo et al. JP HO7309785 A, Eng Trans (Year: 1995).*
Li H (CN 104479465 A), 2015, Eng. Trans (Year: 2015).*
Ames et al., "Structure of the Triterpenes: an Interrelationship between the Lupeol and the ß-Amyrin Series," Nature, 164:1090-1091 (1949).
Halawa et al., "Chemical Constituents of Jojoba Oil and Insecticidal Activity Against *Schistocerca gregaria* and Biochemical Effect on Albino Rats," J. Egypt Soc. Toxicol., 36: 77-87 (2007).
International Search Report for International Application No. PCT/SE2017/051273, dated Feb. 27, 2018.
Purcaro et al., "Characterisation of minor components in vegetable oil by comprehensive gas chromatography with dual detection," Food Chemistry, 212: 730-738 (2016).
Van Boven et al., "Content and Composition of Free Sterols and Free Fatty Alcohols in Jojoba Oil," J. Agric. Food Chem., 45: 1180-1184 (1997).
Verleyen et al., "Analysis of Free and Esterified Sterols in Vegetable Oils," JAOCS, 79(2): 117-122 (2002).
Written Opinion of the International Searching Authority for International Application No. PCT/SE2017/051273, dated Feb. 27, 2018.

* cited by examiner

PETROLATUM SUBSTITUTION PREPARATION

This application is a divisional of U.S. application Ser. No. 16/466,086, filed on Jun. 3, 2019, which is a national stage filing under 35 U.S.C. § 371 of International Application No. PCT/SE2017/051273, filed on Dec. 14, 2017, which claims the benefit of the filing date of Swedish Patent Application No. 1651664-3, filed on Dec. 16, 2016, each of which is incorporated herein by reference in its entirety.

TECHNICAL FIELD

The present invention relates to a preparation for the replacement or substitution of petrolatum as well as the use and manufacture of the preparation.

BACKGROUND

Petrolatum is a well-known product with a lot of different uses within many different areas.

Petrolatum is well known since a long time ago. For instance, U.S. Pat. No. 127,568 dated 1872 describes the manufacture of Vaseline from residuums of petroleum which have not been vaporized in distillation. The term Vaseline is in U.S. Pat. No. 127,568 described as a thick oily pasty substance semi-solid in appearance with a melting point of 30-43° C.

Beauty and personal care formulations are often emulsions of an oil phase (emollient) dispersed in an aqueous medium. The choice of oil phase is important for determining the characteristics of the formulation, such as skin feel, consistency and stability. The oil phase may be composed of mineral oils such as paraffin oil or petrolatum, esters of various types, triglycerides and/or silicone oils. A review of technologies used as emollients in skin care is given by Alander (Chemical and Physical Properties of Emollients, in Treatment of Dry Skin Syndrome, The Art and Science of Moisturizers, Loden, M & Maibach, H I, Springer-Verlag, 2012).

Emollients and oils are also used in products intended for hair care and cleansing applications, such as shampoos, conditioners and shower gels. In this case the oil is dispersed in a solution of surfactants, with or without additional stabilizer and emulsifiers.

High melting, waxy materials are used in beauty and personal care applications such as lipsticks, lip-balms, pencils and foundations to impart consistency and stabilize dispersions of pigments and minerals.

The oil phase in the aforementioned applications needs to be stable, safe to use and compatible with other ingredients used in the formulation. Mineral oils and synthetic hydrocarbons fulfill these requirements. However, they are non-renewable and contribute to higher levels of greenhouse gas emissions (Våg, Marby et al, J Synth Lubr 19-1, 2002, 39-57). It is therefore of interest to find substitutes for both liquid, semi-solid and waxy mineral oils used in the beauty and personal care industry.

EP 2011483 (Walter Rau Neusser Öl and Fett AG) discloses a cosmetic or pharmaceutical composition comprising a mixture of a medium chain triglyceride with a long-chain triglyceride. The long-chain triglyceride is characterized by having a content of fatty acids longer than or equal to 20 carbons, which is 10-100 wt %. The composition should have an iodine value of less than 30 and preferably less than 2, stating that the composition is essentially fully saturated. The use of medium chain triglycerides is undesirable in this type of application, due to several aspects: short chain triglycerides are less stable against hydrolysis, releasing fatty acids with undesired flavor profiles and higher irritation potential. Medium chain triglycerides are shorter than long-chain triglycerides, i.e. shorter than 20 carbons. The manufacture of medium chain triglycerides is also complex, using high temperatures and catalysts that are damaging to the environment. There is therefore a need for preparations, while showing petrolatum-like properties, that also are less irritant and require less energy consuming processes in their manufacture. Further it is desirable to have a preparation which is more stable against hydrolysis.

EP 0661924 (Aarhus Oliefabrik A/S) discloses a preparation for use as a substitute for petrolatum, comprising an oxidation resistant glyceride oil and/or a liquid wax, a solid wax, a structuring fat and (optionally) other functional additives. The oxidation stable glyceride oil is derived from well-known vegetable oil sources and can be partially hydrogenated, partially liquid, fractionated or interesterified. The liquid wax is for example, jojoba oil. The solid wax is beeswax, candelilla or carnauba wax or other similar natural waxes. The structuring fat is a hydrogenated vegetable oil which is solid at room temperature, optionally interesterified or fractionated. The preparation requires the use of either a solid wax or a liquid wax, and if the solid fat is omitted, a liquid wax must be present. Liquid waxes such as jojoba oil are scarce and expensive. The solid waxes such as candelilla and carnauba come from natural sources which are diminishing due to over-exploitation. A preparation which is similar to petrolatum without the use of the waxes is therefore desirable.

US 2003/0207971 discloses preparations comprising mixtures of an oil and a high-melting wax forming a gel that can be used as an emollient. The oil can be any of a vegetable oil, an animal fat or a petroleum derived oil. The wax should have an average molecular weight between 700-3000 Da and a melting point between 37.7° C. to 165.6° C. The wax should be added in concentrations between 2 to 60% by weight. The wax can further be selected from any of natural, petrochemical or synthetic waxes. The gel preparation may contain, in addition to the liquid oil, a hydrogenated vegetable oil. The proposed preparations are either based on a petroleum source (ozokerite and other), a petroleum derived synthetic wax or a natural wax which is derived from a diminishing or non-renewable source (candelilla wax).

A preparation that is similar to petrolatum without the use of petroleum derived waxes or waxes from diminishing sources is therefore desirable.

SUMMARY

It is an object of the present invention to obviate at least some of the disadvantages in the prior art and provide an improved substitute for petrolatum.

It has surprisingly been found that mixing preparation of an oil thickening agent, a structuring forming agent, and a phytosterol or ester thereof and an emollient, will give petrolatum-like properties. The preparation can optionally also contain a high melting wax at low concentration. This preparation is suitable for use in beauty and personal care applications such as skin care creams and lotions, body-butters, lip treatments as well as decorative cosmetics. It is also useful as an ingredient in hair care applications such as shampoos, rinse-off conditioners as well as leave-on hair styling products. The preparation can also be used in shower products as an emollient and re-lipidising/moisturizing ingredient.

In general, the present preparation can replace petrolatum in any application. Petrolatum can be replaced entirely or partially by the present preparation at least by some of the embodiments of the preparation described herein.

In a first aspect there is provided a petrolatum substitute preparation comprising 1-20 wt % of at least one oil thickening agent, 7-40 wt % of at least one structuring agent, 0.5-10 wt % of at least one phytosterol or ester thereof, and 30-92 wt % of at least one emollient, wherein the preparation has a melting point of 35° C. or more.

Further aspects and embodiments are defined in the appended claims, which are specifically incorporated herein by reference.

One advantage is that the preparation according to the invention can be made renewable compared to traditional petrolatum. It is also an advantage that the use of natural waxes from over-exploited sources is minimized.

Further the preparation is less irritant.

The preparation is more stable to oxidation compared to other petrolatum substitute preparations known in the art.

Moreover, the preparation has improved moisture barrier properties. In an in vitro moisture barrier test, the measured apparent water evaporation rate is similar to or only slightly inferior compared to petrolatum. Compositions based on prior art, comprises only a structure forming agent in oil, and are not as effective in forming a moisture barrier.

Another advantage is that the preparation is less energy requiring to manufacture, in that the manufacturing processes are done at lower temperatures and in fewer steps compared to petrolatum.

DETAILED DESCRIPTION

Before the invention is disclosed and described in detail, it is to be understood that this invention is not limited to particular compounds, configurations, method steps, substrates, and materials disclosed herein as such compounds, configurations, method steps, substrates, and materials may vary somewhat. It is also to be understood that the terminology employed herein is used for the purpose of describing particular embodiments only and is not intended to be limiting since the scope of the present invention is limited only by the appended claims and equivalents thereof.

It must be noted that, as used in this specification and the appended claims, the singular forms "a", "an" and "the" include plural referents unless the context clearly dictates otherwise.

If nothing else is defined, any terms and scientific terminology used herein are intended to have the meanings commonly understood by those of skill in the art to which this invention pertains.

The term "about" as used in the description and the claims denotes certain interval around a value, ±10% of the value. Thus the term about 20 means that the value can be in the interval 18-22.

Oil as used herein throughout the description and the claims is any chemical substance which is a viscous liquid at room temperature and is both hydrophobic and lipophilic, e.g. not soluble in water but soluble in ether.

Oxidation resistance as used throughout this specification and the claims is the ability to withstand oxidation and is measured as the oxidative stability index at 110° C. according to AOCS Cd 12b-92(m).

Melting point as used throughout this specification and the claims is the endset measured with differential scanning calorimetry (DSC).

Iodine value as used throughout this specification and the claims is measured according to IUPAC 2.205.

Saponification value as used throughout this specification and the claims is measured according to IUPAC 2.202.

Room temperature as used throughout the description and the claims denotes a temperature of about 20-25° C.

All percentages are calculated by weight unless otherwise indicated.

In a first aspect there is provided a petrolatum substitute preparation, comprising 1-20 wt % of at least one oil thickening agent, 7-40 wt % of at least one structuring agent, 0.5-10 wt % of at least one phytosterol or ester thereof, and 30-92 wt % of at least one emollient, wherein the preparation has a melting point of 35° C. or more.

The melting point of 35° C. or more is to ensure some solids to remain on the skin when applied.

The preparation comprises at least one oil thickening agent. In one embodiment the at least one oil thickening agent comprises at least one isoprenoid or poly-isoprenoid compound. In one embodiment the at least one isoprenoid fraction is saturated. In an alternative embodiment the at least one isoprenoid fraction is unsaturated.

In one embodiment the at least one oil thickening agent comprises at least one vegetable oil. In one embodiment the at least one vegetable oil is dimerized. In one embodiment the at least one vegetable oil is polymerized. Dimerized and polymerized vegetable oils are renewable and natural substances that are effective in increasing the viscosity of the oil.

In one embodiment the at least one oil thickening agent comprises at least one latex. In one embodiment the at least one latex comprises at least one selected from the group consisting of gutta percha, natural rubber latex and balata. Gutta percha and balata are latex obtained from specific trees.

In one embodiment the at least one oil thickening agent comprises at least one hydrocarbon from shea butter. In one embodiment the at least one oil thickening agent consists of at least one hydrocarbon from shea butter. This has the advantage that it is less prone to cause allergic reactions. The hydrocarbon from shea butter is free from proteins which are normally found in natural rubber latex and does not cause allergies or sensitization. Further it does not comprise any fossil raw materials.

In one embodiment the at least one oil thickening agent comprises at least one selected from the group consisting of polyisobutenes, polydecenes, polyolefins, synthetic polyesters, hydrophobically modified acrylates, and polyamides. Synthetically derived oligomers and polymers offer possibilities to increase viscosities of the oil phases above the levels reachable with other alternatives and increase the stickiness of the composition in order to influence deposition on the skin.

In one embodiment the oil thickener comprises a mixture of oil thickeners selected from the above mentioned groups. By mixing oil thickeners from different groups, the properties of the composition may further be optimized for different applications, by influencing, for example, the interaction with the surfaces of skin and hair. In a preferred embodiment, the oil thickeners are selected from dimerized vegetable oils and hydrocarbons derived from shea butter, as this combination is renewable and natural in contrast to the synthetic alternatives.

The oil thickening agent is often diluted in an emollient to ease the handling. The oil thickening agent may be added as 100% ingredient or in form of a diluted ingredient. When diluted, it may be diluted in an emollient. Thus the weight percentage of the oil thickening agent is herein calculated as its weight of only the oil thickening agent even if it is diluted in an emollient prior to use and prior to mixing with other ingredients.

Thus in one embodiment the oil thickening agent comprises a mixture of any one of the compounds mentioned above as "oil thickening agent" or being a constituent in the "oil thickening agent".

The preparation further comprises at least one structuring agent. In one embodiment the at least one structuring agent comprises at least one nonpolar hard component. In one embodiment the at least one structuring agent consists of at least one nonpolar hard component. In one embodiment the at least one nonpolar hard component comprises at least one selected from the group consisting of a triglyceride with a melting point of at least 35° C., a wax ester with a melting point of at least 35° C., a wax with a melting point of at least 35° C., and a long chain (C20-C60) hydrocarbon with a melting point of at least 35° C. Long chain hydrocarbon in this context and in view of the melting point is defined as a C20-C60. In one embodiment the hydrocarbon is from a renewable source.

In one embodiment the at least one structuring agent comprises a semipolar hard component. In one embodiment the at least one semipolar hard component comprises at least one selected from the group consisting of a fatty acid with a melting point of at least 35° C., a fatty alcohol with a melting point of at least 35° C., mono- and/or diglycerides of fatty acids with a melting point of at least 35° C., fatty acid partial esters of polyglycerol, sorbides, sorbitans, sorbitol, sucrose, pentaerythritol and methylolpropane, hydrogenated castor oil with a melting point of at least 35° C., and castor oil fatty acids with a melting point of at least 35° C.

In one embodiment the at least one oil thickening agent is a semi-polar hard component comprising at least one hydroxy stearic acid. In an alternative embodiment the oil thickening agent is at least one semi-polar hard component comprising other mono-hydroxyl fatty acids with a melting point above 35° C., or mixes thereof.

In one embodiment the at least one structuring agent comprises at least one selected from the group consisting of a triglyceride, a saturated triglyceride, a semi-solid triglyceride, a high melting wax, a wax ester, and a hydrocarbon.

In one embodiment the at least one structuring agent comprises at least one nonpolar hard component and the at least one nonpolar hard component comprises at least one selected from the group consisting of a triglyceride with a melting point of at least 45° C., a wax ester with a melting point of at least 45° C., a natural wax with a melting point of at least 45° C., and a long chain (C20 to C60) hydrocarbon with a melting point of at least 45° C.

In one embodiment the at least one structuring agent comprises at least one nonpolar hard component and the at least one nonpolar hard component comprises at least one selected from the group consisting of a triglyceride with a melting point of at least 55° C., a wax ester with a melting point of at least 55° C., a natural wax with a melting point of at least 55° C., and a long chain (C20 to C60) hydrocarbon with a melting point of at least 55° C.

The preparation further comprises at least one phytosterol or ester thereof. In one embodiment the at least one phytosterol or ester thereof comprises at least one selected from a triterpene and a triterpene ester. In one embodiment the at least one phytosterol or ester thereof comprises triterpenes esterified with at least one selected from the group consisting of long chain fatty acids (C13-C31), cinnamic acid, acetic acid, and derivatives of cinnamic acid.

In one embodiment the derivatives of cinnamic acid is at least one selected from the group consisting of ferulic acid, sinapic acid, p-coumaric acid, 3-phenylpropanoic acid, 3-cyclohexylpropanoic acid and caffeic acid. In one embodiment the at least one phytosterol or ester thereof comprises at least one selected from lupeol and amyrin. In one embodiment the at least one phytosterol or ester thereof comprises beta-sitosterol, campesterol, stigmasterol, lanosterol, cholesterol, betulinol, and betulinic acid. In one embodiment the at least one phytosterol or ester thereof comprises at least one phytosterol ester. In one embodiment the at least one phytosterol or ester thereof consists of at least one phytosterol ester.

Triterpenes and phytosterols easily form liquid crystals. The triterpenes, phytosterols and their respective esters mentioned above contribute to the barrier properties of the composition by being able to form liquid crystals as well as solid crystals in the composition, slowing down and blocking the diffusion of water through the barrier. Thus ingredients forming liquid and solid crystals contribute to improved barrier properties and are included in one embodiment.

The preparation further comprises at least one emollient. In one embodiment the at least one emollient is at least one selected from the group consisting of a liquid vegetable oil with a melting point of 25° C. or below, a vegetable butter with a melting point of 35° C. or below, an at least partly hydrogenated vegetable oil with a melting point of 35° C. or below, an interesterified vegetable oil with a melting point of 35° C. or below, an ester with a melting point of 35° C. or below, a synthetic triglyceride with a melting point of 35° C. or below, and a synthetic polyol ester with a melting point of 35° C. or below. In one embodiment the vegetable butter is at least one selected from shea butter, cocoa butter, mango butter, illipe butter, murumuru butter, cupuacu butter and Shorea robusta seed butter. In one embodiment the at least one vegetable butter is hydrogenated.

In one embodiment the oxidative stability index at 110° C. determined according to AOCS Cd 12b-92(m) exceeds 40 hours. It is an advantage of the invention that the preparation is highly oxidation resistant. As oxidative stability is an important factor when using an emollient, the choice of ingredients is important. A refined vegetable oil such as a soy bean oil or rape seed oil, typically have less than 10 hours @ 110° C. in oxidative stability index. Using high stability oils such as Lipex Bassol C increases the oxidative stability to above 40 hours but there are other oils exceeding 100 hours which can be used as well according to the invention. In addition, anti-oxidants can be added to the product to increase oxidative stability. In one embodiment the preparation comprises at least one anti-oxidant. The invention makes it possible to select ingredients which are highly oxidation resistant so that the entire preparation thereby becomes highly oxidation resistant.

In one embodiment the at least one oil thickening agent increases the viscosity of the preparation, but does not increase the viscoelasticity of the preparation. This means that the viscosity increases when the oil thickening agent is added, but the viscoelasticity does not increase when the oil thickening agent is added.

In one embodiment the preparation is viscoelastic. The viscoelasticity typically comes from a component which is not the oil thickening agent. Examples include but are not limited to non-hydrocarbon oil and compounds originating from shea.

In one embodiment the preparation comprises sorbitan tristearate. This has the advantage of providing a better appearance and it gives a more translucent preparation. The improved appearance is an advantage for various surface coatings as well as for many cosmetic applications.

In one further embodiment the preparation comprises 1-20 wt % of the at least one oil thickening agent. In still one further embodiment the preparation comprises 1-20 wt % of a combination of oil thickening agents. By mixing oil thickeners from different groups, the properties of the composition may further be optimized for different applications, by influencing, for example, the interaction with the surfaces of skin and hair. In a preferred embodiment, the oil thickeners are selected from dimerized vegetable oils and hydrocarbons derived from shea butter, as this combination is renewable and natural in contrast to the synthetic alternatives. In one further embodiment the preparation has a melting point of at least 35° C., 40° C. In another further embodiment the preparation has a melting point of at least 42° C. In yet another embodiment the preparation has a melting point of at least 46° C., such as 50° C., 53° C. or even 54° C., 56° C., 60° C., 70° C., 76° C. or even 80° C., 90° C.

Any combination of the at least one oil thickening agent, the at least one structuring agent, the at least one phytosterol or ester thereof, and the at least one emollient as mentioned herein are encompassed.

The preparation can be utilized for a lot of different applications. Since the preparation is intended to replace petrolatum it can be used in all applications where petrolatum currently is used. In one embodiment the preparation fully replaces petrolatum and in an alternative embodiment the preparation replaces petrolatum partially, such as for 1 wt %, 5 wt %, 10 wt %, 20 wt %, 30 wt %, 40 wt %, 50 wt %, 60 wt %, 70 wt %, 80 wt %, 90 wt %, 95 wt %, 97 wt %, 99 wt % or even for 99.9 wt %. In one embodiment the preparation is used in an amount of 1-100 wt % in the final formulation. Use of 100% of the petrolatum substitute preparation as described herein in the final formulation corresponds to 100% replacement of petrolatum in the final formulation, i.e. the petrolatum replacement preparation is replacing petrolatum to 100%. 100% replacement of petrolatum means that all petrolatum in the final product is replaced, but the final product normally also comprises other ingredients so that the total amount of the preparation in the final product is less than 100%.

In one embodiment the petrolatum substitute preparation as described herein is intended for use as an ingredient in at least one selected from the group consisting of a cosmetic formulation, a beauty formulation, a personal care formulation, a skin care formulation, a hair care formulation, a lip care formulation, a coloured cosmetic formulation, a sun care formulation, a lotion, an ointment, a cream, and a soft gel capsule, a coating, a conditioner, a lubricant, a cleaner, a trolley lubricant, a food grade grease, a gear lube formulation, a pharmaceutical composition, a car wax, and a furniture wax.

In a second aspect there is provided the use of the preparation as described in any embodiments herein as an ingredient in at least one selected from the group consisting of a cosmetic formulation, a beauty formulation, a personal care formulation, a skin care formulation, a hair care formulation, a lip care formulation, a colored cosmetic formulation, a sun care formulation, a lotion, an ointment, a cream, and a soft gel capsule, coating, a conditioner, a lubricant, a cleaner, a trolley lubricant, a food grade grease, a gear lube formulation, a pharmaceutical composition, a car wax, and a furniture wax.

There is further provided the use of the preparation as described in any of the embodiments above as an ingredient in at least one product selected from the group consisting of a lotion, an ointment, a cream, and a soft gel capsule. In one embodiment the preparation is used in an amount of 1-100 wt % in the final product. In one embodiment the preparation is used in an amount of 1-99.9 wt % in the final product. In another embodiment the preparation is used in an amount of 5-20 wt % in the final product. 100 wt % of the final product means that the product consists only of the petrolatum replacement according to the invention, in such an embodiment pure replacement preparation can replace for instance pure Vaseline. Often the amount of the preparation according to the invention constitutes a lower amount in the final product, such as the mentioned 5-20 wt %.

In a third aspect there is provided a formulation comprising the preparation as described in any of the embodiments above, wherein the formulation is at least one selected from the group consisting of a cosmetic formulation, a beauty formulation, a personal care formulation, a skin care formulation, a hair care formulation, a lip care formulation, a coloured cosmetic formulation, a sun care formulation, a lotion, an ointment, a cream, and a soft gel capsule, coating, a conditioner, a lubricant, a cleaner, a trolley lubricant, a food grade grease, a gear lube formulation, a pharmaceutical composition, a car wax, and a furniture wax. In one embodiment the amount of preparation in the formulation is 1-100 wt %. In one embodiment the formulation is a barrier forming formulation intended to come into contact with the skin of a human. It is intended to be applied on the skin of a human user.

Often it is desired that the formulation applied to the skin of a human should be fast spreading and fast absorbing. If such properties are desired a low viscous and polar ester should be used. Examples of such esters are Lipex SheaLight, IPP, IPM, MCT. One such example is given in Example 6.

There is further provided use of a petrolatum substitute preparation as described herein in a formulation intended to come into contact with the skin of a human, in order to reduce the transepidermal water loss (TEWL). In a further embodiment the preparation is used in a formulation intended to come in contact with the skin of a human, in order to increase the moisture level in the skin, which may also in some preferred embodiments also reduce the transepidermal water loss (TEWL) in the same embodiment. In one embodiment the petrolatum substitute preparation is used in a formulation in an amount of 1-100 wt %. In one embodiment the preparation is used in a formulation in an amount of 5-20 wt %. 100 wt % would correspond to pure petrolatum substitute preparation, which can be used, but most often the petrolatum substitute preparation constitutes a fraction of the final product, in which it replaces at least a part of the petrolatum in the final product.

In a fourth aspect there is provided a barrier forming formulation intended to come into contact with the skin of a human, wherein the barrier forming formulation comprises the petrolatum substitute preparation as described in any of the embodiments herein. In one embodiment the preparation is present in the formulation in an amount of 1-100 wt %. In one embodiment the barrier forming formulation comprises the preparation wherein the preparation comprises a trisaturated triglyceride, a natural hydrocarbon and an ester. In this particular embodiment the structuring agent is a trisaturated triglyceride, the oil thickening agent is a hydrocarbon, such as a natural hydrocarbon, and the emollient is an ester. The preparation further comprises a phytosterol or ester thereof. Further examples of barrier forming formulations comprising the preparation as described in any of the embodiments herein are disclosed below.

One example of a barrier forming formulation comprising the petrolatum substitute preparation is wherein the at least one oil thickening agent comprises a natural hydrocarbon, the at least one structuring agent comprises a non-polar hard component, the at least one phytosterol or ester thereof comprises a triterpene or ester thereof, and the at least one emollient. The natural hydrocarbon originating from shea is in one embodiment in the range of 0.5 to 8%.

A further embodiment of a barrier forming formulation comprising the petrolatum substitute preparation is wherein the at least one oil thickening agent comprises a natural hydrocarbon, the at least one structuring agent comprises a triglyceride, the at least one phytosterol or ester thereof comprises a triterpene from Shea or ester thereof, and the at least one emollient comprises liquid glycerides from Shea oil. The amount of triterpenes and ester thereof originating from shea is in one embodiment in the range of about 0.5-10 wt % of the preparation, or about 0.5-7 wt %.

A further embodiment of a barrier forming formulation comprising the petrolatum substitute preparation is wherein the least one oil thickening agent comprises a natural hydrocarbon, the at least one structuring agent comprises a non-polar hard component, the at least one phytosterol or ester thereof comprises a triterpene or ester thereof, and the at least one emollient. The non polar hard components comprise wax esters such as cetearyl behenate, triglycerides such as fully hydrogenated vegetable oils, hydrocarbons such as paraffin, waxes such as sun flower wax and combinations thereof. The amount of structuring agent is in one embodiment in the interval of about 7-40 wt %, or such as about 7-25 wt %.

A further embodiment of a barrier forming formulation comprising the petrolatum substitute preparation is wherein the at least one oil thickening agent comprises a natural hydrocarbon, the at least one structuring agent comprises a non-polar hard component, the at least one phytosterol or ester thereof comprises a triterpene or ester thereof, and the at least one emollient comprises a partially hydrogenated Shea butter. The amount of partially hydrogenated shea butter is in one embodiment in the interval 5 to 93 wt % of the preparation.

A further embodiment of a barrier forming formulation comprising the petrolatum substitute preparation is wherein the least one oil thickening agent comprises a natural hydrocarbon, the at least one structuring agent comprises a non-polar hard component, the at least one phytosterol or ester thereof comprises a triterpene or ester thereof, and the at least one emollient. The non polar hard components comprise wax esters such as cetearyl behenate, triglycerides such as fully hydrogenated vegetable oils, hydrocarbons such as paraffin, waxes such as sun flower wax and combinations thereof. The amount of structuring agent (e.g. non-polar hard component) is in one embodiment in the interval 7-40 wt %, the amount of phytosterols (e.g. triterpenes) and ester thereof originating from shea is in the range 0.5-10 wt % of the preparation and the natural hydrocarbon originating from shea (oil thickening agent) is in the range of 0.5 to 8%. Further embodiments are wherein the amount of structuring agent is in the interval 10-20 wt %, the amount of phytosterols (e.g. triterpenes) and ester thereof originating from shea is in the range 2-6 wt % of the preparation and the natural hydrocarbon originating from shea is in the range of 2 to 8 wt %. Even further embodiments are wherein the amount of structuring agent is in the interval 7-15 wt %, the amount of phytosterols (eg triterpenes) and ester thereof originating from shea is in the range 2-6 wt % of the preparation and the natural hydrocarbon originating from shea is in the range of 2 to 8 wt %.

A further embodiment of a barrier forming formulation comprising the petrolatum substitute preparation is wherein the least one oil thickening agent comprises a natural hydrocarbon, the at least one structuring agent comprises a non-polar hard component, the at least one phytosterol or ester thereof comprises a triterpene or ester thereof, and the at least one emollient. The non polar hard components comprise wax esters such as cetearyl behenate, triglycerides such as fully hydrogenated vegetable oils, hydrocarbons such as paraffin, waxes such as sun flower wax and combinations thereof. The amount of structuring agent is in one embodiment in the interval 10-20 wt %. The amount of triterpenes and ester thereof originating from shea is in one embodiment at least 2% of the preparation. The natural hydrocarbon originating from shea is in one embodiment at least 2% of preparation. However, the amount of phytosterols and natural hydrocarbon are in a range between 4 to 12%.

A further embodiment of a barrier forming formulation comprising the petrolatum substitute preparation is wherein the least one oil thickening agent comprises a natural hydrocarbon, the at least one structuring agent comprises a non-polar hard component, the at least one phytosterol or ester thereof comprises a triterpene or ester thereof, and the at least one emollient. The non polar hard components comprise wax esters such as cetearyl behenate, triglycerides such as fully hydrogenated vegetable oils, hydrocarbons such as paraffin, waxes such as sun flower wax and combinations thereof. The amount of structuring agent is in one embodiment in the interval 7-15 wt %. The amount of triterpenes and ester thereof originating from shea is in one embodiment at least 2% of the preparation. The natural hydrocarbon originating from shea is in one embodiment at least 2% of preparation. However, the amount of phytosterols and natural hydrocarbon are in a range between 7 to 12%.

In a fifth aspect there is provided a method of manufacturing a preparation as described in any of the embodiments above, comprising the steps of mixing the ingredients, i.e. 1-20 wt % of at least one oil thickening agent, 7-40 wt % of at least one structuring agent, 0.5-10 wt % of at least one phytosterol or ester thereof, and 30-92 wt % of at least one emollient, wherein the preparation has a melting point of 35° C. or more.

The method may in further embodiments comprise the steps of heating the preparation gently during the mixing until all ingredients have melted. In further embodiments the ingredients are heated to a temperature in the interval 60-100° C. during mixing, such as 60° C., 70° C., 80° C., 90° C., 95° C., 97° C. or even 99° C. In one embodiment the method further comprises interesterification. In one embodiment the method further comprises hydrogenation. The steps may be carried out in various orders. In one embodiment the method further comprises deodorization. The ingredients are in one embodiment mixed and then deodorized. In another embodiment the ingredients are deodorized and then mixed. In yet another embodiment deodorizing of at least some of the ingredients before the mixing is combined with deodorizing of the ingredients after mixing. In one embodiment the deodorization is carried out after the mixing of the ingredients. In one embodiment the deodorization is carried out before the mixing of the ingredients. The steps can be carried out in various orders, for instance as mentioned above the deodorization step can also be carried out on the ingredients before the mixing, instead of after the mixing.

EXAMPLES

Throughout the examples as well as the description and the claims all percentages are calculated by weight unless otherwise clearly indicated.

Raw Materials

High Melting Components:

Akofine R: FH Rapeseed triglyceride oil (FH RSTO) is characterized by having <2 in iodine value. The fatty acid profile is stearic acid (40-50%), behenic acid (40-50%), 3-7% of arachidic fatty acids and below 5% of other.

FH Vegetable triglyceride oil (FH VTO) is characterized by having <2 in iodine value and a saponification value of 170-230. The fatty acid preparation comprises palmitic acid (40-60 wt %) and stearic acid (40-50 wt %) and below 10 wt % of other fatty acids.

Wax ester 1: Cetearyl behenate, CAS 92797-30-3, a C34-C46 long chain ester with a melting point of 56-65° C.

Wax ester 2: Cetyl stearate, CAS 124487-61-2, a C34 to C40 long chain ester with a melting point of 54-59° C.

Liquid Vegetable Oils

Lipex Bassol C: The liquid triglyceride oil (VEG oil) is characterized by having >50 in iodine value and a saponification value of between 170-230. The amount of unsaturated fatty acids >35 wt %.

Lipex 205: The liquid shea butter is characterized by having >70 in iodine value and a saponification value of about 183. The amount of unsaturated fatty acids is >65 wt %.

Lipex SheaLight: The liquid shea butter ester is characterized by being a blend of ethyl-oleate (45-65 wt %), ethyl-linolate (5-10 wt %), ethyl stearate (20-30 wt %), ethyl palmitate (3-7 wt %) and a triterpene ester content of 5-13 wt %.

Semisolid Vegetable Fats

Lipex 512 is a partially hydrogenated shea butter with a melting point of 34° C.

The partly hydrogenated triglyceride oil (PHTO) is characterized of having an iodine value of 40-70 and saponification value of 170-250. The amount of unsaturated fatty acids >35 wt %. The melting point is above 30 to 45° C.

Natural Hydrocarbon Oil (NHO).

A refined Shea butter was melted to 60° C. and then cooled to 40° C. 1 kg of shea butter was blended with 4 liters of acetone at 40° C. The blend was cooled to 10° C. so the natural hydrocarbon precipitated without oil precipitation. The blend was filtered to separate the oil from the natural hydrocarbon. The filter cake weighed 42 grams of most of it was natural hydrocarbons with some traces of high melting fats and acetone. 150 grams of Lipex 205 (a refined shea butter oil) was added to the filter cake and then the acetone was removed at 60° C., 100 mbar pressure. The resulting mixture was refined and deodorised according to standard procedures. The unsaponifiable matter and capillary viscosity at 50° C. were determined to 21 wt % and 170 cSt, respectively.

Summary of ingoing materials (in wt %):

| | Structuring agents | | Phytosterols | | Oil thickening agent | | |
| | | | Triterpene | | | | |
| | Non polar hard component | Semi-polar hard component | esters and triterpene alcohols | Other phytosterol/ phytosterol esters | Hydrocarbons from shea | Other oil thickening agent | Emollients |
|---|---|---|---|---|---|---|---|
| Akofine R ™ | 100 | 0 | 0 | 0 | 0 | 0 | 0 |
| Cetearyl behenate | 100 | 0 | 0 | 0 | 0 | 0 | 0 |
| Sunflower wax | 100 | 0 | 0 | 0 | 0 | 0 | 0 |
| Sorbitan tristearate | 0 | 100 | 0 | 0 | 0 | 0 | 0 |
| NHO | 0 | 0 | 7 | 0 | 16 | 0 | 77 |
| Lipex 205 ™ | 0 | 0 | 9 | 0 | 0 | 0 | 91 |
| Lipex 512 ™ | 0 | 0 | 9 | 0 | 0 | 0 | 91 |
| Lipex Bassol C ™ | 0 | 0 | 0 | 0 | 0 | 0 | 100 |
| Soybean oil | 0 | 0 | 0 | 0 | 0 | 0 | 100 |
| Akomed R ™ | 0 | 0 | 0 | 0 | 0 | 0 | 100 |
| Lipex SheaLight ™ | 0 | 0 | 9 | 0 | 0 | 0 | 91 |
| Isopropyl palmitate (IPP) | 0 | 0 | 0 | 0 | 0 | 0 | 100 |
| Paraffin wax | 100 | 0 | 0 | 0 | 0 | 0 | 0 |

Paraffin wax SP-674, Strahl & Pitsch Inc—USA. A paraffin wax with a melting point of 70° C. and contains mainly carbon chain lengths between 30-35.

Petrolatum: White Protopet 1 SH, Sonneborn

This petrolatum is a very soft type of petrolatum.

Petrolatum K:

For all barrier tests a commercial Klövers Vaseline, produced by Unilever was used. Petrolatum Klöver is 100% petrolatum based. This can be considered as hard type of a petrolatum.

EXPERIMENTAL PROCEDURES

Blending Procedure:

Prior to the blending all ingredients were warmed at 80° C. until completely melted. The blends were made according to Table 1-14, in 40 g batches in a 100 ml beaker. Each blend was then divided in four, and added to small glass jars with 10 grams in each. Three of the glass jars were cooled at room temperature in a cooling cabinet or with stirring until reaching the end temperature. After reaching the end temperature the jars were kept at 20° C.

The texture measurements were performed with a texture analyser TA.XT.Plus.

The DSC tests were performed using a Mettler-Toledo DSC-822e. 3-10 mg product was added to an aluminium capsule and sealed. The filled capsule was transferred into the DSC unit. The sample was heated to 90° C. (5° C./min). After 2 minutes at 90° C. the capsule was cooled to −30 C (5° C./min) and kept for 20 minutes at −30° C. Finally, the sample was heated to 90° C. (5° C./min). The melting point (endset) is defined as endset of the last peak during the last step.

Experiment 1

The soft petrolatum was melted at 80° C. until completely melted. The samples were then cooled to room temperature and stored at 20° C. until further use or minimum 72 hours.

TABLE 1

| The recipe | [gram] |
| --- | --- |
| Petrolatum - White Protopet 1 SH | 40 g |
| Resulting composition | [wt %] |

Experiment 2

A Hard Petrolatum was melted at 80° C. until completely melted. The samples were then cooled to room temperature and stored at 20° C. until further use or minimum 72 hours.

TABLE 2

| The recipe | [gram] |
| --- | --- |
| Petrolatum Klöver | 40 g |

Experiment 3

A blend of the ingredients according to the recipe in Table 3 was made by blending all ingredients at 80° C. until completely melted. The samples were then cooled to room temperature and stored at 20° C. until further use or minimum 72 hours.

TABLE 3

| The recipe | [gram] |
| --- | --- |
| Akofine R | 4 |
| Lipex Bassol C | 36 |
| Sum | 40 |
| Resulting composition | [wt %] |
| Non polar hard component (structuring agent) | 10 |
| Semi polar hard component (structuring agent) | 0 |
| oil thickening agent | 0 |

TABLE 3-continued

| phytosterol or ester thereof | 0 |
| --- | --- |
| emollient | 90 |

Experiment 4

A blend of the ingredients according to the recipe in Table 4 was made by blending all ingredients at 80° C. until completely melted. The samples were then cooled to room temperature and stored at 20° C. until further use or minimum 72 hours.

TABLE 4

| The recipe | [gram] |
| --- | --- |
| Akofine R | 4 |
| Lipex Bassol C | 34.8 |
| Cetearyl behenate | 1.2 |
| Sum | 40 |
| Resulting composition | [wt %] |
| Non polar hard component (structuring agent) | 13 |
| Semi polar hard component (structuring agent) | 0 |
| oil thickening agent | 0 |
| phytosterol or ester thereof | 0 |
| emollient | 87 |

Experiment 5

A blend of the ingredients according to the recipe in Table 5 was made by blending all ingredients at 80° C. until completely melted. The samples were then cooled to room temperature and stored at 20° C. until further use or minimum 72 hours.

TABLE 5

| The recipe | [gram] |
| --- | --- |
| Akofine R | 4 |
| Lipex Bassol C | 34.8 |
| Sunflower wax | 1.2 |
| Sum | 40 |
| Resulting composition | [wt %] |
| Non polar hard component (structuring agent) | 13 |
| Semi polar hard component (structuring agent) | 0 |
| oil thickening agent | 0 |
| phytosterol or ester thereof | 0 |
| emollient | 87 |

Experiment 6

A blend of the ingredients according to the recipe in Table 6 was made by blending all ingredients at 80° C. until completely melted. The samples were then cooled to room temperature and stored at 20° C. until further use or minimum 72 hours.

TABLE 6

| The recipe | [gram] |
|---|---|
| Lipex SheaLight | 17.6 |
| Lipex Bassol C | 4.4 |
| NHO | 12 |
| Akofine R | 6 |
| Sum | 40 |

| Resulting composition | [wt %] |
|---|---|
| Non polar hard component (structuring agent) | 15 |
| Semi polar hard component (structuring agent) | 0 |
| oil thickening agent | 5 |
| phytosterol or ester thereof | 5 |
| Emollient | 75 |

This preparation contains a blend of Lipex SheaLight (44 wt %), Trisaturated triglycerides (15 wt %), hydrogenated vegetable oil and natural hydrocarbon oil (30 wt %). The amount of natural hydrocarbon in the blend was 6 wt %. The sensory properties of the blend are very light and resembles that of petrolatum.

Experiment 7

A blend of the ingredients according to the recipe in Table 7 was made by blending all ingredients at 80° C. until completely melted. The samples were then cooled to room temperature and stored at 20° C. until further use or minimum 72 hours.

TABLE 7

| The recipe | [gram] |
|---|---|
| Lipex Bassol C | 16 |
| NHO | 20 |
| Akofine R | 4 |
| Sum | 40 |

| Resulting composition | [wt %] |
|---|---|
| Non polar hard component (structuring agent) | 10 |
| Semi polar hard component (structuring agent) | 0 |
| oil thickening agent | 8 |
| phytosterol or ester thereof | 4 |
| emollient emollient | 78 |

Experiment 8

A blend of the ingredients according to the recipe in Table 8 was made by blending all ingredients at 80° C. until completely melted. The samples were then cooled to room temperature and stored at 20° C. until further use or minimum 72 hours.

TABLE 8

| The recipe | [gram] |
|---|---|
| Lipex SheaLight | 13 |
| Lipex Bassol C | 13 |

TABLE 8-continued

| | |
|---|---|
| NHO | 6 |
| Akofine R | 8 |
| Sum | 40 |

| Resulting composition | [wt %] |
|---|---|
| Non polar hard component (structuring agent) | 20 |
| Semi polar hard component (structuring agent) | 0 |
| oil thickening agent | 2 |
| phytosterol or ester thereof | 3 |
| Emollient | 75 |

Experiment 9

A blend of the ingredients according to the recipe in Table 9 was made by blending all ingredients at 80° C. until completely melted. The samples were then cooled to room temperature and stored at 20° C. until further use or minimum 72 hours.

TABLE 9

| The recipe | [gram] |
|---|---|
| Akofine R | 4 |
| Lipex Bassol C | 24.8 |
| Cetearyl behenate | 1.2 |
| NHO | 10 |
| Sum | 40 |

| Resulting composition | [wt %] |
|---|---|
| Non polar hard component (structuring agent) | 13 |
| Semi polar hard component (structuring agent) | 0 |
| oil thickening agent | 4 |
| phytosterol or ester thereof | 2 |
| emollient | 81 |

Experiment 10

A blend of the ingredients according to the recipe in Table 10 was made by blending all ingredients at 80° C. until completely melted. The samples were then cooled to room temperature and stored at 20° C. until further use or minimum 72 hours.

TABLE 10

| The recipe | [gram] |
|---|---|
| Cetearyl behenate | 2.5 |
| Paraffin | 2.5 |
| Lipex Bassol C | 27 |
| NHO | 8 |
| Sum | 40 |

| Resulting composition | [wt %] |
|---|---|
| Non polar hard component (structuring agent) | 13 |

TABLE 10-continued

| | |
|---|---|
| Semi polar hard component (structuring agent) | 0 |
| oil thickening agent | 3 |
| phytosterol or ester thereof | 2 |
| emollient | 82 |

Experiment 11

A blend of the ingredients according to the recipe in Table 11 was made by blending all ingredients at 80° C. until completely melted. The samples were then cooled to room temperature and stored at 20° C. until further use or minimum 72 hours.

TABLE 11

| The recipe | [gram] |
|---|---|
| Akofine R | 4 |
| Lipex Bassol C | 24.8 |
| Sunflower wax | 1.2 |
| NHO | 10 |
| Sum | 40 |

| Resulting composition | [wt %] |
|---|---|
| Non polar hard component (structuring agent) | 13 |
| Semi polar hard component (structuring agent) | 0 |
| oil thickening agent | 4 |
| phytosterol or ester thereof | 2 |
| emollient | 81 |

Experiment 12

A blend of the ingredients according to the recipe in Table 12 was made by blending all ingredients at 80° C. until completely melted. The samples were then cooled to room temperature and stored at 20° C. until further use or minimum 72 hours.

TABLE 12

| The recipe | [gram] |
|---|---|
| Cetaryl behenate | 4 |
| Lipex Bassol C | 24 |
| NHO | 12 |
| Sum | 40 |

| Resulting composition | [wt %] |
|---|---|
| Non polar hard component (structuring agent) | 10 |
| Semi polar hard component (structuring agent) | 0 |
| oil thickening agent | 5 |
| phytosterol or ester thereof | 2 |
| emollient | 83 |

Experiment 13

A blend of the ingredients according to the recipe in Table 13 was made by blending all ingredients at 80° C. until completely melted. The samples were then cooled to room temperature and stored at 20° C. until further use or minimum 72 hours.

TABLE 13

| The recipe | [gram] |
|---|---|
| Akofine R | 4 |
| Lipex 512 | 26.8 |
| NHO | 8 |
| Sorbitan tristearate | 1.2 |
| Sum | 40 |

| Resulting in | [wt %] |
|---|---|
| Non polar hard component (structuring agent) | 10 |
| Semi polar hard component (structuring agent) | 3 |
| oil thickening agent | 2 |
| phytosterol or ester thereof (esters) | 6 |
| Emollient | 79 |

Experiment 14

A blend of the ingredients according to the recipe in Table 14 was made by blending all ingredients at 80° C. until completely melted. The samples were then cooled to room temperature and stored at 20° C. until further use or minimum 72 hours.

TABLE 14

| The recipe | [gram] |
|---|---|
| Akofine R | 4 |
| Lipex Bassol C | 33.5 |
| NHO | 2.5 |
| Sum | 40 |

| Resulting composition | [wt %] |
|---|---|
| Non polar hard component (structuring agent) | 10 |
| Semi polar hard component (structuring agent) | 0 |
| oil thickening agent | 1 |
| phytosterol or ester thereof | 0.4 |
| emollient | 88.6 |

Physicochemical Measurements:

Samples from experiments 1, 2, 6, and 8 were analyzed with texture analyser and samples 1-14 were analyzed with DSC.

3-10 mg of each sample was added to aluminum caps and sealed. The sealed caps then were added to the DSC and a program going from 90° C. to −30° C. and up again, 5° C./minute was used to analyse the end set temperature.

| Exp Name | DSC Endset (° C.) |
|---|---|
| 1 | 71 |
| 2 | 76 |
| 3 | 57 |
| 4 | 56 |
| 5 | 62 |
| 6 | 57 |

-continued

| Exp Name | DSC Endset (° C.) |
|---|---|
| 7 | 57 |
| 8 | 58 |
| 9 | 56 |
| 10 | 63 |
| 11 | 60 |
| 12 | 59 |
| 13 | 58 |
| 14 | 57 |

The hardness was measured at 20° C. using a texture analyser TA.XT.Plus. where a 4 mm cylindrical steel probe was used to penetrate the samples in jars 10 mm at a speed of 5 mm/s.

Table Texture

| Exp Name | DSC Onset Crystallization (° C.) | DSC Endset (° C.) | Hardness [gram] |
|---|---|---|---|
| 1 | 54.9 | 71.3 | 17 |
| 2 | 66.7 | 75.6 | 78 |
| 8 | 42.1 | 58.4 | 28 |
| 6 | 39.3 | 56.5 | 22 |

Barrier Tests.
0.7 Grams of Lipids at 30° C.

Selected oils, esters and veg oil blends were evaluated as barriers of moisture.

8 grams of water was added to a small beaker. The area of the top of the beaker was 9 cm$^2$. The headspace was measured to 1 cm, up to the lid of the beaker. A filter paper was put on top of the beaker and taped around the beaker in order to keep it steady.

The oils and esters were heated to 80° C. and 0.7 grams were added to the filter paper, corresponding to a layer thickness of approximately 0.8 mm. The beakers were transferred into a cabinet with a temperature of 30° C. The weight of each beaker was measured at predetermined intervals in order to evaluate the rate of water loss. The reported values represent the average water loss per hour from time zero.

| Experiment No. | mg water/hour/cm$^2$ 22 h | 45 h |
|---|---|---|
| 2 | 0.4 | 0.5 |
| 3 | 3.4 | 3.7 |
| 4 | 2.3 | 2.4 |
| 5 | 2.3 | 2.5 |
| 7 | 0.7 | 0.6 |
| 9 | 1.3 | 1.5 |
| 10 | 0.9 | 1.0 |
| 11 | 0.8 | 1.0 |
| 12 | 0.4 | 0.5 |
| 13 | 0.7 | 0.7 |
| 14 | 2.4 | 2.5 |

Experiment 15, Oil in Water Emulsions

Two formulations were prepared.

Each phase was prepared separately according to Table 14 F1 and 14 F2. A Stephan blender was used for homogenization. Phase A was first added to the Stephan blender and then during stirring phase B and finally phase C was added. The formulation was allowed to be homogenized for 30 minutes. The products were transferred to a beaker and allowed to cool at room temperature. A lid was added to the beaker and then stored for two weeks at room temperature. No sign of separation was seen. The samples were then evaluated with respect to barrier function.

Formulation 1 (Batch Size 500 g)

TABLE 15

| F1 | | |
|---|---|---|
| | | Grams |
| Phase A, Temperature 75° C. | | |
| 1. | Aqua | 351.50 |
| 2. | Carrageenan | 1.00 |
| 3. | Xantan Gum | 1.00 |
| 4. | Glycerin | 20.00 |
| 5. | Disodium EDTA | 1.00 |
| Phase B, Temperature 75° C. | | |
| 6. | Sodium Stearoyl Glutamate | 15.00 |
| 7. | Cetearyl Alcohol | 10.00 |
| 8. | Glyceryl Stearate SE | 10.00 |
| 9. | Preparation from experiment 8 | 85.00 |
| Phase C, Temperature 35° C. | | |
| 10. | Triethanolamine | 0.50 |
| 11. | Phenoxyethanol, Ethylhexylglycerin | 5.00 |

Formulation 2 (Batch Size 500 g)

TABLE 15

| F2 | | |
|---|---|---|
| | | Grams |
| Phase A, Temperature 75° C. | | |
| 1. | Aqua | 351.50 |
| 2. | Carrageenan | 1.00 |
| 3. | Xantan Gum | 1.00 |
| 4. | Glycerin | 20.00 |
| 5. | Disodium EDTA | 1.00 |
| Phase B, Temperature 75° C. | | |
| 6. | Sodium Stearoyl Glutamate | 15.00 |
| 7. | Cetearyl Alcohol | 10.00 |
| 8. | Glyceryl Stearate SE | 10.00 |
| 9. | Petrolatum, experiment-1 | 85.00 |
| Phase C, Temperature 35° C. | | |
| 10. | Triethanolamine | 0.50 |
| 11. | Phenoxyethanol, Ethylhexylglycerin | 5.00 |

Barrier Test 2, 0.5 Grams of Lipids at 30° C.

The two oil in water emulsions prepared were evaluated as barrier of moisture.

8 grams of water was added to a small beaker. The area of the beaker was 9 cm$^2$. The headspace was measure to 1 cm, up to the lid of the beaker. A filter paper was put on top of the beaker and taped around the beaker in order keep steady.

0.5 grams of the formulations were added to the filter paper, corresponding to an initial layer thickness of approximately 0.5 mm. After evaporation of the water of the formulation, this corresponds approximately to a layer thickness of 167 μm. The beakers were transferred into a cabinet with a temperature of 30° C. The weight of each beaker was measured in order to evaluate water losses.

Two samples of each formulation was tested.

TABLE 15

| | F3 | | | |
|---|---|---|---|---|
| | mg water/hour/cm² | | | |
| | 2 hours | 6 hours | 22 hours | 46 hours |
| Formulation 1, Replicate 1 | 18.8 | 8.6 | 3.9 | 2.9 |
| Formulation 1, Replicate 2 | 18.6 | 8.7 | 4.2 | 3.2 |
| Formulation 2, Replicate 1 | 14.7 | 9.1 | 4.7 | 3.9 |
| Formulation 2, Replicate 2 | 18.6 | 8.7 | 4.2 | 3.2 |

The values at 46 hours show an average evaporation rate of 3.1 mg water/hour/cm² for the preparation comprising the petrolatum replacement according to Experiment 8. The average evaporation rate for the formulation with petrolatum (Experiment 1) was 3.6 mg water/hour/cm². It is concluded that the formulation including Experiment 8 has equal or better barrier properties compared to petrolatum.

Comments to the Results

Experiment 2 is the petrolatum and is used as a reference for excellent occlusivity. The lower evaporation rate indicates improved potential for barriers. Experiments 3-5 and 14 are references where the evaporation rate is 5-8 times higher than petrolatum, thus not considered as giving satisfactory barrier or occlusivity potential. These preparations contain waxes and/or high melting triglycerides but not phytosterols or oil thickening agents in concentrations according to the invention. Experiment 6 and 8 contains a very low viscous and highly polar ester, Lipex SheaLight, which is known to not give barrier effects, but instead gives fast spreading and absorbing properties. The results indicate that the lower viscosity and higher polarity lead to lower barrier properties. By combining trisaturated triglycerides with a natural hydrocarbon and an ester, improved sensory properties with improved barrier properties was found. Especially Experiments 7, 12 and 13 and 15 show a particularly good barrier effect, similar to petrolatum.

All the described alternative embodiments above or parts of an embodiment can be freely combined without departing from the inventive idea as long as the combination is not contradictory.

Other features and uses of the invention and their associated advantages will be evident to a person skilled in the art upon reading the description and the examples.

It is to be understood that this invention is not limited to the particular embodiments shown here. The embodiments are provided for illustrative purposes and are not intended to limit the scope of the invention since the scope of the present invention is limited only by the appended claims and equivalents thereof.

The invention claimed is:

1. A petrolatum substitute preparation comprising
   1-20 wt % of at least one oil thickening agent comprising at least one hydrocarbon from shea butter,
   7-40 wt % of at least one structuring agent,
   0.5-10 wt % of at least one phytosterol or ester thereof, and
   30-92 wt % of at least one emollient,
   wherein the preparation has a melting point of at least 35° C.;
   wherein the at least one oil thickening agent comprises at least one vegetable oil;
   further wherein the at least one vegetable oil is dimerized.

2. The preparation according to claim 1, wherein the at least one oil thickening agent comprises at least one isoprenoid compound.

3. The preparation according to claim 2, wherein the at least one isoprenoid fraction is saturated.

4. The preparation according to claim 2, wherein the at least one isoprenoid fraction is unsaturated.

5. The preparation according to claim 1, wherein the at least one oil thickening agent comprises at least one latex.

6. The preparation according to claim 5, wherein the at least one latex comprises at least one latex selected from the group consisting of gutta percha, natural latex and balata.

7. The preparation according to claim 1, wherein the at least one oil thickening agent consists of at least one hydrocarbon from shea butter.

8. The preparation according to claim 1, wherein the at least one oil thickening agent comprises at least one thickening agent selected from the group consisting of polyisobutenes and polydecenes.

9. The preparation according to claim 1, wherein the at least one structuring agent comprises at least one nonpolar hard component.

10. The preparation according to claim 9, wherein the at least one nonpolar hard component comprises at least one nonpolar hard component selected from the group consisting of a triglyceride with a melting point of at least 35° C., a wax ester with a melting point of at least 35° C., a natural wax with a melting point of at least 35° C., and a long chain (C20 to C60) hydrocarbon with a melting point of at least 35° C.

11. The preparation according to claim 9, wherein the at least one nonpolar hard component comprises at least one nonpolar hard component selected from the group consisting of a triglyceride with a melting point of at least 45° C., a wax ester with a melting point of at least 45° C., a natural wax with a melting point of at least 45° C., and a long chain (C20 to C60) hydrocarbon with a melting point of at least 45° C.

12. The preparation according to claim 9, wherein the at least one nonpolar hard component comprises at least one nonpolar hard component selected from the group consisting of a triglyceride with a melting point of at least 55° C., a wax ester with a melting point of at least 55° C., a natural wax with a melting point of at least 55° C., and a long chain (C20 to C60) hydrocarbon with a melting point of at least 55° C.

13. The preparation according to claim 1, wherein the at least one structuring agent comprises a semipolar hard component.

14. The preparation according to claim 13, wherein the semipolar hard component comprises at least one semipolar hard component selected from the group consisting of a fatty acid with a melting point of at least 35° C., a fatty alcohol with a melting point of at least 35° C., mono- and/or diglycerides of fatty acids with a melting point of at least 35° C., fatty acid partial esters of polyglycerol, sorbides, sorbitans, sorbitol, sucrose, pentaerythritol and methylolpropane, hydrogenated castor oil or a hydroxyl stearic acid with a melting point of at least 35° C., and castor oil fatty acids with a melting point of at least 35° C.

15. The preparation according to claim 1, wherein the at least one structuring agent comprises at least one structuring agent selected from the group consisting of a triglyceride, a saturated triglyceride, a semi-solid triglyceride, a high melting wax, a wax ester, and a hydrocarbon.

16. The preparation according to claim 1, wherein the at least one phytosterol or ester thereof comprises at least one phytosterol or ester selected from a triterpene and a triterpene ester.

17. The preparation according to claim 1, wherein the at least one phytosterol or ester thereof comprises triterpene esters esterified with at least one selected phytosterol or ester from the group consisting of long chain fatty acids (C13-C31), cinnamic acid, acetic acid, and derivatives of cinnamic acid.

18. The preparation according to claim 17, wherein the derivatives of cinnamic acid is at least one derivative selected from the group consisting of ferulic acid, sinapic acid, p-coumaric acid, 3-phenylpropanoic acid, 3-cyclohexylpropanoic acid and caffeic acid.

19. The preparation according to claim 1, wherein the at least one phytosterol or ester thereof comprises at least one selected from lupeol, amyrin, beta-sitosterol, campesterol, stigmasterol, lanosterol, cholesterol, betulinol, and betulinic acid.

20. The preparation according to claim 1, wherein the at least one phytosterol or ester thereof comprises at least one phytosterol ester.

21. The preparation according to claim 1, wherein the at least one emollient is at least one selected from the group consisting of a liquid vegetable oil with a melting point of 25° C. or below, a vegetable butter with a melting point of 35° C. or below, an at least partly hydrogenated vegetable oil with a melting point of 35° C. or below, an interesterified vegetable oil with a melting point of 35° C. or below, an ester with a melting point of 35° C. or below, a synthetic triglyceride with a melting point of 35° C. or below, and a synthetic polyol ester with a melting point of 35° C. or below.

22. The preparation according to claim 21, wherein the vegetable butter is at least one selected from shea butter, cocoa butter, mango butter, illipe butter, murumuru butter, cupuacu butter, and Shorea robusta seed butter.

23. The preparation according to claim 22, wherein the vegetable butter is hydrogenated.

24. The preparation according to claim 1, wherein the oxidative stability index at 110° C. determined according to American Oil Chemists' Society (AOCS) Cd 12b-92(m) exceeds 40 hours.

25. The preparation according to claim 1, wherein the at least one oil thickening agent increases the viscosity of the preparation, but does not increase the viscoelasticity of the preparation.

26. The preparation according to claim 1, wherein the preparation is viscoelastic.

27. The preparation according to claim 1, wherein the preparation comprises sorbitan tristearate.

28. The preparation according to claim 1, wherein the preparation comprises 10-20 wt % of the at least one oil thickening agent.

29. The preparation according to claim 1, wherein the preparation has a melting point of at least 40° C.

30. The preparation according to claim 1, wherein the preparation has a melting point of at least 46° C.

31. The preparation according to claim 1, wherein the preparation is an ingredient in at least one formulation selected from the group consisting of a cosmetic formulation, a beauty formulation, a personal care formulation, a skin care formulation, a hair care formulation, a lip care formulation, a coloured cosmetic formulation, a sun care formulation, a lotion, an ointment, a cream, and a soft gel capsule, coating, a conditioner, a lubricant, a cleaner, a trolley lubricant, a food grade grease, a gear lube formulation, a pharmaceutical preparation, a car wax, and a furniture wax.

32. The preparation according to claim 31, wherein the at least one formulation comprises 1-100 wt % of the preparation.

33. A method of reducing the transepidermal water loss (TEWL) of skin comprising administering to the skin in need thereof an effective amount of the preparation according to claim 1.

34. The method according to claim 33, wherein the preparation is used in a formulation in an amount of 1-100 wt %.

35. A method of increasing the moisture content in the skin comprising administering to the skin in need thereof an effective amount of the preparation according to claim 1.

36. The petrolatum substitute preparation of claim 1, wherein the melting point of the preparation ranges from 35° C.-55° C.

37. A method of manufacturing a petrolatum substitute preparation comprising:
 1-20 wt % of at least one oil thickening agent comprising at least one hydrocarbon from shea butter,
 7-40 wt % of at least one structuring agent,
 0.5-10 wt % of at least one phytosterol or ester thereof, and
 30-92 wt % of at least one emollient, and
 a melting point of at least 35° C.,
 the method comprising the steps of mixing the ingredients and further comprising interesterification.

38. A petrolatum substitute preparation comprising
 1-20 wt % of at least one oil thickening agent,
 7-40 wt % of at least one structuring agent,
 1-10 wt % of at least one phytosterol or ester thereof, and
 30-92 wt % of at least one emollient,
wherein the preparation has a melting point of at least 35° C.;
wherein the at least one oil thickening agent comprises at least one vegetable oil;
further wherein the at least one vegetable oil is dimerized.

39. The petrolatum substitute preparation of claim 38, wherein the melting point of the preparation ranges from 35° C.-55° C.

40. A petrolatum substitute preparation comprising
 1-20 wt % of at least one oil thickening agent comprising at least one hydrocarbon from shea butter,
 7-40 wt % of at least one structuring agent,
 0.5-11 wt % of at least one phytosterol or ester thereof,
 30-92 wt % of at least one emollient,
wherein the preparation has a melting point of at least 35° C.;
wherein the at least one oil thickening agent comprises at least one vegetable oil;
further wherein the at least one vegetable oil is polymerized.

41. A method of manufacturing a petrolatum substitute preparation comprising:
 1-20 wt % of at least one oil thickening agent comprising at least one hydrocarbon from shea butter,
 7-40 wt % of at least one structuring agent,
 0.5-12 wt % of at least one phytosterol or ester thereof, and
 30-92 wt % of at least one emollient, and
 a melting point of at least 35° C.,
 the method comprising the steps of mixing the ingredients and further comprising hydrogenation.

42. A method of manufacturing a petrolatum substitute preparation comprising:
 1-20 wt % of at least one oil thickening agent comprising at least one hydrocarbon from shea butter,
 7-40 wt % of at least one structuring agent, 0.5-13 wt % of at least one phytosterol or ester thereof, and 30-92 wt % of at least one emollient, and a melting point of at least 35° C., the method comprising the steps of mixing the ingredients and further comprising deodorization.

43. The method according to claim 42, wherein the deodorization is carried out before the mixing of the ingredients.

44. The method according to claim 42, wherein the deodorization is carried out after the mixing of the ingredients.

* * * * *